(12) United States Patent
Chen et al.

US012167720B2

(10) Patent No.: US 12,167,720 B2
(45) Date of Patent: Dec. 17, 2024

(54) STRUCTURE AND METHOD FOR PROMOTING MICROALGAE GROWTH

(71) Applicants: THE REGENTS OF THE UNIVERSITY OF CALIFORNIA, La Jolla, CA (US); UNIVERSITY OF CAMBRIDGE, Cambridge (GB)

(72) Inventors: Shaochen Chen, San Diego, CA (US); Dimitri Deheyn, Cardiff-by-the-Sea, CA (US); Shangting You, La Jolla, CA (US); Daniel Wangpraseurt, Cambridge (GB); Silvia Vignolini, Cambridge (GB)

(73) Assignee: The Regents of the University of California, Oakland, CA (US)

( * ) Notice: Subject to any disclaimer, the term of this patent is extended or adjusted under 35 U.S.C. 154(b) by 315 days.

(21) Appl. No.: 17/639,223

(22) PCT Filed: Aug. 28, 2020

(86) PCT No.: PCT/US2020/048605
§ 371 (c)(1),
(2) Date: Feb. 28, 2022

(87) PCT Pub. No.: WO2021/041962
PCT Pub. Date: Mar. 4, 2021

(65) Prior Publication Data
US 2022/0322644 A1 Oct. 13, 2022

Related U.S. Application Data

(60) Provisional application No. 62/893,162, filed on Aug. 28, 2019.

(51) Int. Cl.
*A01K 61/70* (2017.01)
*B29C 64/129* (2017.01)
(Continued)

(52) U.S. Cl.
CPC .......... *A01K 61/70* (2017.01); *B29C 64/129* (2017.08); *B29C 64/245* (2017.08);
(Continued)

(58) Field of Classification Search
CPC .... A01K 61/70; B29C 64/129; B29C 64/245; B29C 64/277; B29C 64/286; B33Y 10/00;
(Continued)

(56) References Cited

U.S. PATENT DOCUMENTS 7,997,231 B2    8/2011  Fernandez
2015/0057786 A1*  2/2015  Murphy ................ B41J 2/1752
                                                        700/119
(Continued)

FOREIGN PATENT DOCUMENTS

KR    20110085411    *  7/2011
WO    2016100856 A1    6/2016
(Continued)

OTHER PUBLICATIONS

Wangpraseurt D, Wentzel C, Jacques SL, Wagner M, Ku'hl M., In vivo imaging of coral tissue and skeleton with optical coherence tomography, 2017, J.R. Soc., Interface (Year: 2017).*
(Continued)

*Primary Examiner* — Emmanuel S Luk
*Assistant Examiner* — Victoria Bartlett
(74) *Attorney, Agent, or Firm* — Eleanor Musick; Torrey Pines Law Group PC

(57) ABSTRACT

An artificial structure for promoting microalgae growth includes a 3D-printed structure formed by positioning a printing surface on a movable stage of a 3D bioprinter in contact with a bio-ink that includes a mixture of a pre-polymer material with one or more of cellulose-derived nanocrystals (CNC), and microalgae cells. By projecting
(Continued)

modulated light onto the printing surface while moving the stage, the bio-ink is progressively polymerized to define layers of an artificial coral structure with microalgae cells disposed thereon, where the artificial coral structure is configured to scatter light within the structure.

24 Claims, 13 Drawing Sheets

(51) Int. Cl.

| | | |
|---|---|---|
| *B29C 64/245* | (2017.01) | |
| *B29C 64/286* | (2017.01) | |
| *B29K 1/00* | (2006.01) | |
| *B29K 105/00* | (2006.01) | |
| *B29L 31/00* | (2006.01) | |
| *B33Y 10/00* | (2015.01) | |
| *B33Y 70/10* | (2020.01) | |
| *B33Y 80/00* | (2015.01) | |

(52) U.S. Cl.
CPC ............ *B29C 64/286* (2017.08); *B33Y 10/00* (2014.12); *B33Y 70/10* (2020.01); *B33Y 80/00* (2014.12); *B29K 2001/08* (2013.01); *B29K 2105/0032* (2013.01); *B29K 2105/0073* (2013.01); *B29K 2995/0056* (2013.01); *B29L 2031/702* (2013.01)

(58) Field of Classification Search
CPC .......... B33Y 70/10; B33Y 80/00; C12N 1/12; B29K 2001/08; B29K 2105/0032; B29K 2105/0073; B29K 2995/0056; B29L 2031/702

See application file for complete search history.

(56) References Cited

U.S. PATENT DOCUMENTS

| | | | | |
|---|---|---|---|---|
| 2018/0257297 A1* | 9/2018 | Matheu | ............... | A61L 27/3625 |
| 2020/0109299 A1* | 4/2020 | Qian | ...................... | B33Y 70/00 |
| 2020/0367477 A1* | 11/2020 | Schofield | ............... | C09J 101/08 |

FOREIGN PATENT DOCUMENTS

| | | |
|---|---|---|
| WO | 2017033190 A1 | 3/2017 |
| WO | 2019173637 A1 | 9/2019 |

OTHER PUBLICATIONS

Klinges, D., A new dimension to marine restoration: 3D printing coral reefs, https://news.mongabay.com/2018/08/a-new-dimension-to-marine-restoration-3d-printing-coral reefs/ Aug. 27, 2018 (Aug. 27, 2018), entire document.

PCT/US2020/048605 International Search Report/Written Opinion, Nov. 30, 2020 (7 pages).

* cited by examiner

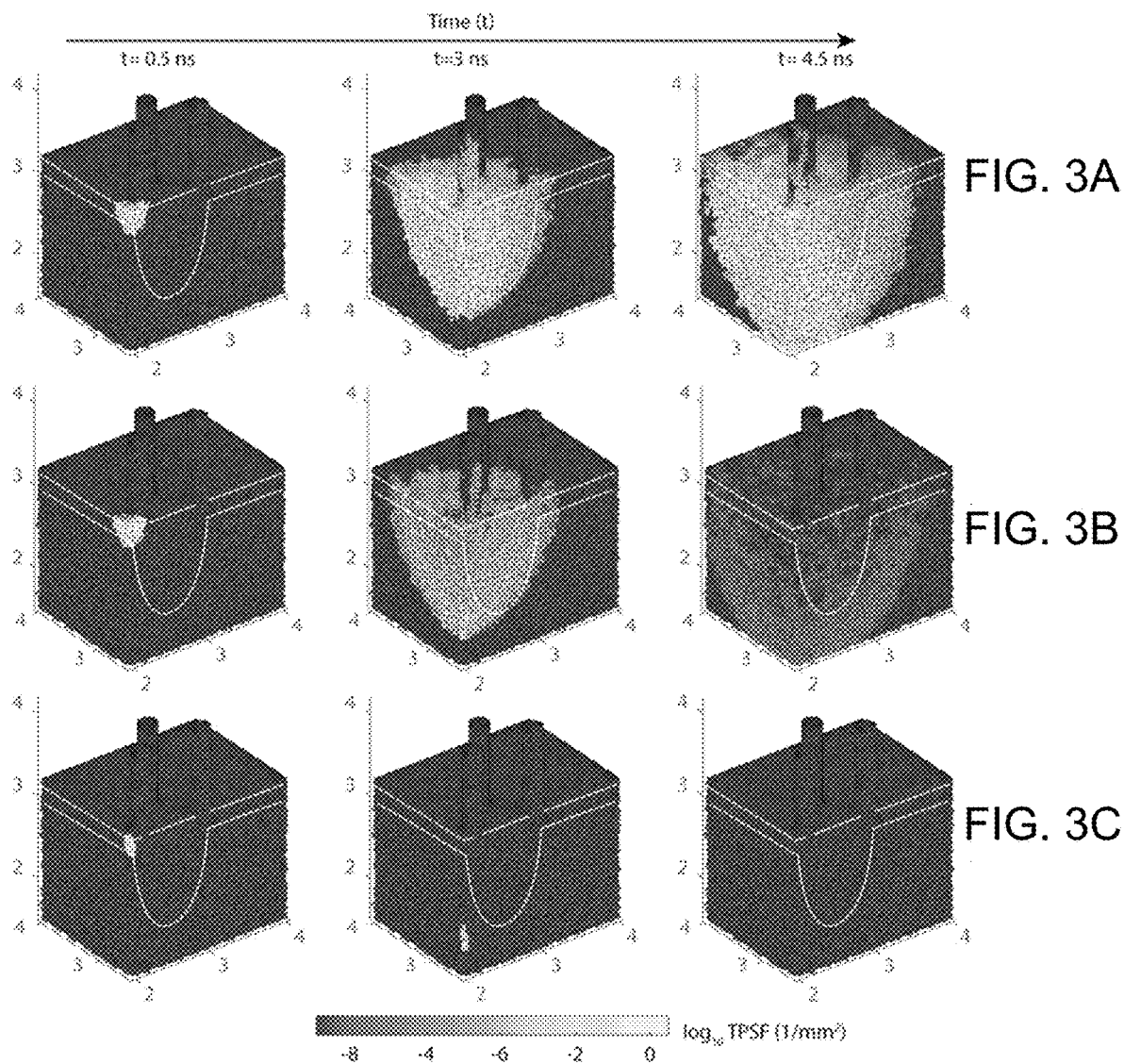

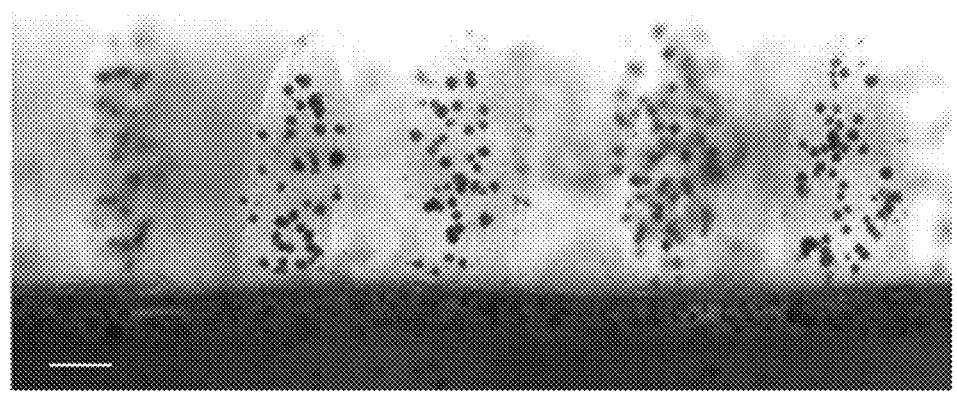
FIG. 6A
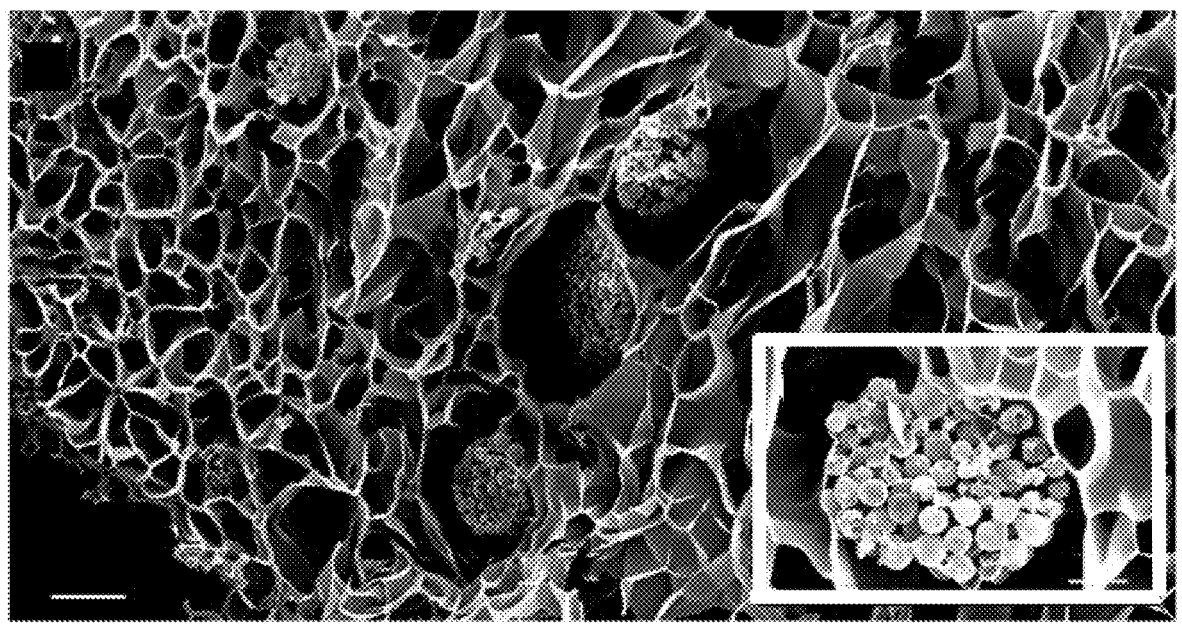
FIG. 6B
FIG. 6C

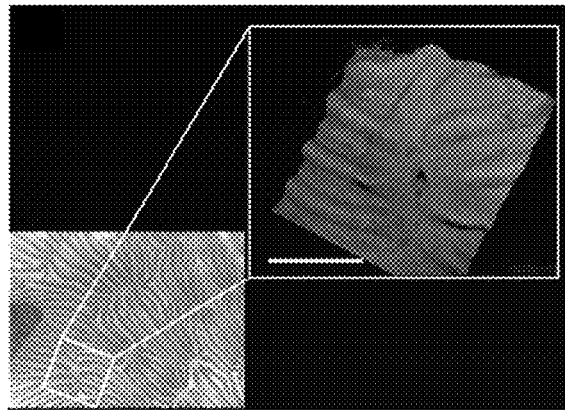
FIG. 7E
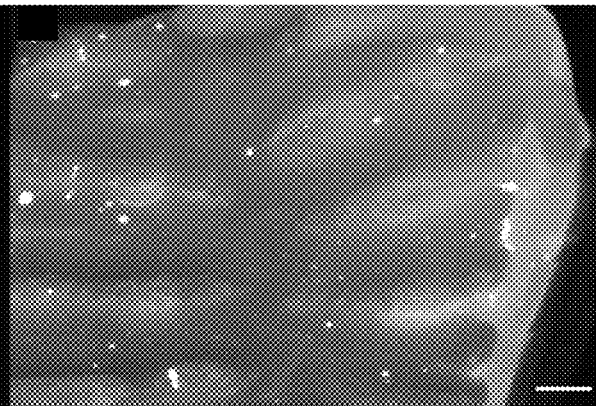
FIG. 7F
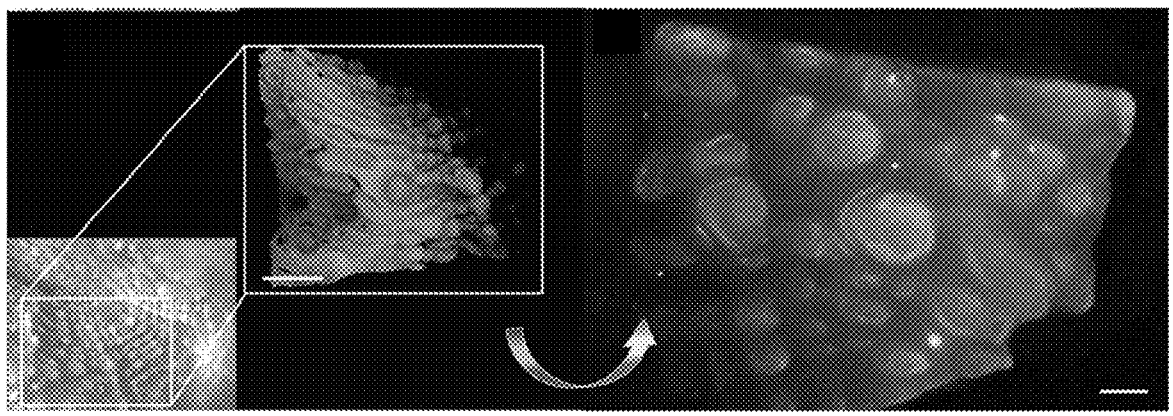
FIG. 7G
FIG. 7H

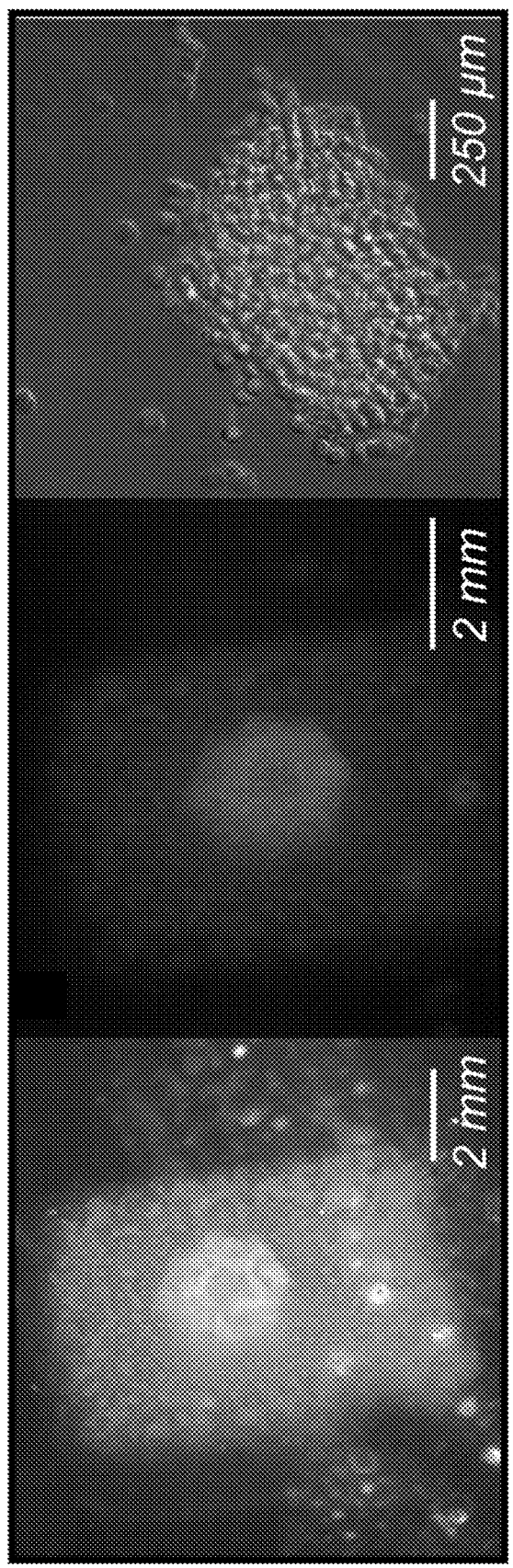

| Platform | Light use efficiency [g mol ph-1] | Max. areal Density [g m-2] | Areal Productivity [g m-2 d-1] | Volumetric Density [w/v] | Maintenance | Water usage | Strain | Scale |
|---|---|---|---|---|---|---|---|---|
| Open pond | - | - | 13.2 | 0.01-0.1% | Very low | Poor | *Chlorella sp.* | Pilot |
| Stirred flask | - | - | - | 0.01-0.1% | Medium | Poor | *M. kaistiae* KAS 603 | Lab |
| Flat panel | 0.22-0.63 | - | 25-27.5 | - | Very high | Medium | *Nannochloropsis sp., Scenedesmus ovalternus* | Pilot |
| Vertical column | 0.55 | - | 0.04-24.4 | 0.05-0.47% | Very high | Medium | *Chlamydomonas reinhardtii, Chlorella sp., Dunaliella tertiolecta* | Pilot |
| Horizontal tubular | - | - | 0.52-3.3 | 0.02-1.2% | Very high | Medium | *Chlorella sorokiniana, Nannochloropsis salina, Phaeodactylum* | Lab |
| Biofilm | 0.63 | 50 | 6 | - | Medium | Good | *Pseudochlorococcum sp.* | Lab |
| Twin layer | 0.31 | 0.6-1.8 | 1.8 | - | Medium | Good | *Isochrysis, Nannochloropsis, Phaeodactylum* | Pilot |
| Polystyrene foam | 0.27 | 25.6 | 2.56 | - | Low | Good | *Chlorella sp.* | Lab |
| Rotating algal disk | 0.9 | - | 20 | 12-15% | Low | Good | *Chlorella sorokiniana* | Lab |
| Algal Turf Scrubber | - | - | 35 | - | Very low | Good | Mixed filamentous | Large-scale |
| Bionic Coral* | 0.37-1.2 | 12.7-62 | 2.55-15.7 | 3.1-3.4% | Very low | Excellent | *M. kaistiae* KAS 603 | Lab |

FIG. 13

STRUCTURE AND METHOD FOR PROMOTING MICROALGAE GROWTH

RELATED APPLICATIONS

This application is a 371 national stage filing of International Application No. PCT/US2020/048605, filed Aug. 28, 2020, which claims the benefit of the priority of U.S. Application No. 62/893,162, filed Aug. 28, 2019, entitled "BIONIC 3D PRINTED CORALS", which is incorporated herein by reference in its entirety.

FIELD OF THE INVENTION

The present invention relates to a method and system for 3D bioprinting of artificial corals and use of 3D-bioprinted synthetic coral structures for enhanced yield of microalgae.

BACKGROUND

Microalgae cultivation has an advancing role in solving limitations in traditional biomass production and markets, including food, feed, energy, emission mitigation, chemicals, biological material, and more. Furthermore, microalgae are considered to be one of the most promising feedstock materials for developing a sustainable supply of commodities, including food and nonfood products. They also produce natural compounds that can be used as functional food ingredients to enhance the nutritional value of foods. Microalgae have also been widely investigated for treatment of wastewater for mitigating the environmental impact of organic discharges from various industries.

Corals are the building blocks of coral reef ecosystems and the primary producers that support coral reef food chains. Certain types of microalgae live in a symbiotic relationship with corals, where the corals provide a habitat for the microalgae to grow, and in return, the algae produce fixed carbon for the coral. Single-celled microalgae consume carbon dioxide and other waste products of their hosts while providing photosynthetic nutrients—with the coral skeleton and tissue structure passing just the right amount of light to benefit their symbiotic algae. With climate change causing sea temperatures to rise and oceans to acidify, coral reefs are dying around the world. The delicate reefs are particularly susceptible to small changes in average temperature and salinity, and as they die, this could also spell disaster for the many marine organisms that call the reefs home.

Symbiotic corals have evolved as a highly optimised photon augmentation system leading to space-efficient microalgal growth and photosynthetic quantum efficiencies that approach theoretical limits. Corals are characterized by an elastic animal tissue hosting microalgae and a light scattering calcium carbonate skeleton that maximizes light delivery towards otherwise shaded algal-containing tissues. Rapid light attenuation due to algal self-shading is a key limiting factor for the upscaling of microalgal cultivation. Coral-inspired light management systems could overcome this limitation and facilitate scalable bioenergy and bioproduct generation as well as heling to mitigate some of the inevitable damage resulting from climate change.

BRIEF SUMMARY

The inventive method and system employ novel bionic corals for enhancing the efficiency of light delivery for converting solar energy into biofuel in the form of algae production. These bionic corals mimic the optical, mechanical and morphological microenvironment of natural corals with a micron resolution, enabling growth of a range of microalgae, from the native symbiotic strain (Symbiodinium) to commercially relevant species (Chlorella), magnifying microalgal productivity per unit volume 10-100 times greater than is possible in liquid culture. Applications include biofuel production in both dedicated stations and dense urban areas and life support systems for space travel, sustainable waste treatment, and food sources.

An artificial structure and method for using the structure for promoting microalgae growth involves creating a 3D-printed structure by positioning a printing surface on a movable stage of a 3D bioprinter in contact with a bio-ink that includes a mixture of a pre-polymer material with one or more of cellulose-derived nanocrystals (CNC), and microalgae cells. By projecting modulated light onto the printing surface while moving the stage, the bio-ink is progressively polymerized to define layers of an artificial coral structure with microalgae cells disposed thereon. The artificial coral structure is configured to scatter light within the structure to optimize exposure of the microalgae for efficient photosynthetic activity.

According to embodiments of the invention, the hybrid photosynthetic biomaterials are produced using a 3D bioprinting platform which mimics morphological features of living coral tissue and the underlying skeleton with micron resolution, including their optical and mechanical properties. The programmable synthetic microenvironment allows for replication of structural and functional traits of the coral-algal symbiosis. The inventive approach defines a new class of bionic materials capable of interacting with living organisms, which can be exploited for the design of next generation photobioreactors as well as potential solutions for coral reef conservation.

The coral-algal symbiosis has evolved a highly optimized photon management system with photosynthetic efficiencies approaching theoretical limits. The inventive method and system provide 3D printed bionic corals capable of growing various types of microalgae with cell densities approaching $10^9$ cells/mL, up to 100 times greater than in liquid culture. The hybrid photosynthetic biomaterials are produced with a 3D bioprinting platform which mimics morphological features of living coral tissue and the underlying skeleton with micron resolution, including their optical and mechanical properties. The programmable synthetic microenvironment thus allows for replicating both structural and functional traits of the coral-algal symbiosis. The approaches described herein relate to a new class of bionic materials capable of interacting with living organisms, that can be exploited for the design of next generation photobioreactors and disruptive approaches for coral reef conservation.

In one aspect of the invention, a method for promoting microalgae growth involves providing an artificial coral structure by disposing a printing surface on a movable stage of a 3D bioprinter, the 3D bioprinter comprising a digital micromirror device configured for modulating light from a light source into patterns defined by a plurality of digital masks, projection optics configured for projecting the modulated light onto a focal plane at the printing surface; contacting the printing surface with at least one bio-ink, wherein the at least one bio-ink comprises a mixture of a pre-polymer material with one or more of cellulose-derived nanocrystals (CNC), and microalgae cells; projecting modulated light onto the printing surface while moving the stage to progressively polymerize the at least one bio-ink to define layers of an artificial coral structure with microalgae cells disposed thereon, wherein the artificial coral structure is configured to scatter light within the structure; placing the artificial coral structure within a cultivation medium; and exposing the artificial coral structure to photosynthesis-inducing radiation. In some embodiments, the at least one bio-ink comprises a mixture of at least one pre-polymer material, a photoinitiator, CNC and microalgae cells. The at least one bio-ink may further comprise artificial seawater and/or a dye configured to limit penetration of polymerizing light into the mixture. In other embodiments, the at least one bio-ink may be a first bio-ink and a second bio-ink, where the first bio-ink is a mixture of the pre-polymer material and CNC and the second bio-ink is a mixture of pre-polymer material and microalgae cells, wherein the first bio-ink is used to print skeletal structures having a plurality of pores and cavities and tissue structures having radially-extending projections. The skeletal structures may include corallite-shaped functional units tuned to scatter photosynthesis-inducing light, and the radially-extending projections may be disposed around a periphery of the corallite-shaped functional units. The second bio-ink may be printed onto the skeletal structures and tissue structures.

In some embodiments, the pre-polymer material may be one or more of polyethylene glycol diacrylate (PEGDA) and gelatin methacrylate (GelMA). The plurality of digital masks may be created from slices of microscopic images of natural coral skeletons and tissues, and may be generated using optical coherence tomography (OCT). The light source preferably emits light within the visible spectra and may be light at 405 nm. The microalgae cells may be one or more of *Marinichlorella kaistiae* and *Symbiodinium* sp.

In another aspect of the invention, an artificial structure for promoting microalgae growth includes a 3D-printed structure formed by disposing a printing surface on a movable stage of a 3D bioprinter, the 3D bioprinter comprising a digital micromirror device configured for modulating light from a light source into patterns defined by a plurality of digital masks, projection optics configured for projecting the modulated light onto a focal plane at the printing surface, contacting the printing surface with at least one bio-ink, wherein the at least one bio-ink comprises a mixture of a pre-polymer material with one or more of cellulose-derived nanocrystals (CNC), and microalgae cells; and projecting modulated light onto the printing surface while moving the stage to progressively polymerize the at least one bio-ink to define layers of an artificial coral structure with microalgae cells disposed thereon, wherein the artificial coral structure is configured to scatter light within the structure.

The high spatial efficiency of the bionic coral system is suitable for the design of compact photobioreactors for algal growth in dense urban areas, or as life support systems for space travel.

BRIEF DESCRIPTION OF THE DRAWINGS

FIGS. 1A and 1B are images generated by optical coherence tomography scanning of coral skeleton and coral tissue, respectively; FIG. 1C is a scanning electron microscopy image of successful 3D printed skeleton replica showing corallites in 1:1 scale relative to the original design; FIG. 1D is a photograph of living bionic coral growing *Symbiodinium* sp. microalgae where the living tissue was printed on top of the skeleton mimic and the bionic coral was cultured for 7 days. Scale bar=1 mm (1B-1F) and 750 µm (1G).

FIG. 2A is a 3D rendering of final bionic coral design; FIG. 2B shows bionic skeletal design optimization with SEM images of the original *Stylophora pistillata* corallite architecture (scale bar=200 µm); FIG. 2C shows a 3D printed intermediate skeleton design (scale bar=300 µm), FIG. 2D shows the final bionic skeleton doped with CNC aggregates (scale bar=100 µm).

FIGS. 3A-3C show a 3D tetrahedral mesh-based Monte Carlo simulation, where light (675 nm) is irradiated over the connecting tissue (red arrow) as a collimated pencil beam. The time-resolved solution of photon migration (temporal point spread function, TPSF [$1/mm^3$]) is shown after 0.5 ns (left column), 3 ns (center column), and 4.5 ns (right column) in a cross-cut view of the 2-layer bionic coral (FIG. 3A), a 1-layer bionic tissue (FIG. 3B) and non-scattering GelMA (FIG. 3C). The microalgal density in the tissue component is identical for all simulations ($\mu_a=15$ $mm^{-1}$).

FIG. 5B plots vertical attenuation of fluence rate ($E_0$ at 675 nm) at the beginning (day 1) and end of the performance test (day 12). FIG. 5C plots net photosynthetic rates at day 5, 8 and 11, where lines represent curve fits. FIG. 5D plots gross photosynthetic rates at day 5 (black) and day 8 (blue).

FIGS. 6A-6C are images of living 3D printed bionic coral, with a horizontal view of 7-day old bioprinted construct, with FIG. 6A showing aggregates of the green microalga *Marinichlorella kaistiae* KAS603 (scale bar=100 µm); FIG. 6B is a SEM image of bionic tissue showing porous tissue scaffolds (scale bar=20 µm); and FIG. 6C (inset) is a close-up of a microalgal aggregate (scale bar=10 µm).

FIGS. 7A-7H provides comparisons of microtopography of corals and 3D bioprinted bionic corals, where FIGS. 7A and 7B show a skeleton of *Pavona cactus*, FIGS. 7C and 7D show *Pocillopora damicornis*, FIGS. 7E and 7F show tissue surface of *Pavona cactus*, and FIGS. 7G and 7H show *Favites flexuosa*.

FIG. 8A shows total transmittance of bionic skeleton with 7% CNC concentration for different slab thicknesses (1-4.5 mm), showing that the high CNC density yields a rough surface (see SEM image in inset, scale bar=40 µm). FIG. 8B plots total transmittance of bionic coral tissue doped with different concentrations of CNC (0-2%). FIG. 8C shows fitting of extrapolation length (ze) for bionic skeleton according to Eq. 2 based on the angular distribution of transmitted light. FIG. 8D plots calculated transport mean free path ($l_t$, µm) and FIG. 8E the absorption length ($l_a$, mm) for bionic skeleton (mean±CI). Extinction length for bionic tissue estimated using Beer-Lambert law (mean±CI) is shown in FIG. 8F.

FIGS. 12A-12C show *Thalassiosira pseudonana* 3D bioprinted culture about 7 days old, where FIG. 12A shows diatoms growing in aggregates that are macroscopically visible (scale bar: 2 mm); FIG. 12B shows chlorophyll fluorescence imaging of the same bioprint (scale bar: 2 mm), and FIG. 12C is a close up of an individual diatom aggregate (scale bar: 250 μm).

FIG. 13 is a table comparing the characteristics of the inventive bionic corals with key microalgal cultivation platforms.

DETAILED DESCRIPTION OF EMBODIMENTS OF THE INVENTION

Figure 1A:
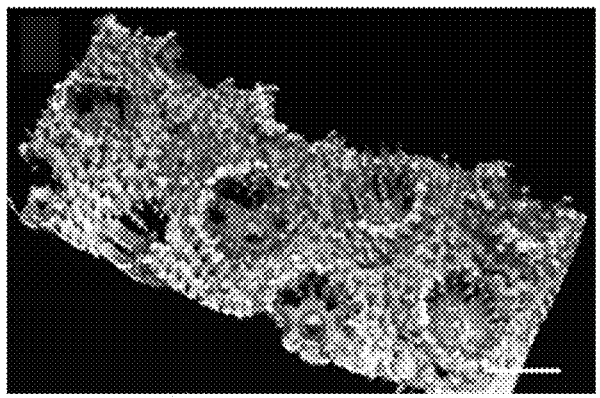
FIGS. 1A-1D are microscope images comparing natural coral with bionic coral fabricated using 3D printing according to the inventive scheme, where
Figure 1B:
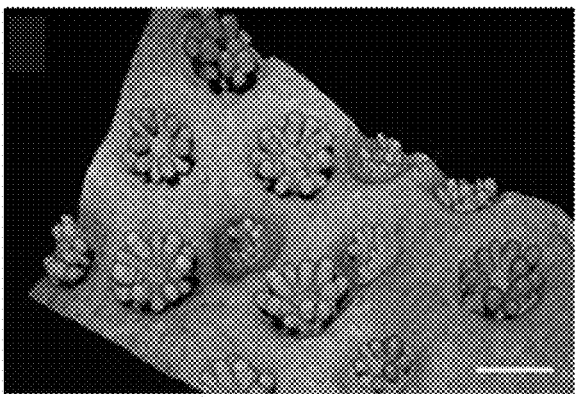
Figure 1C:
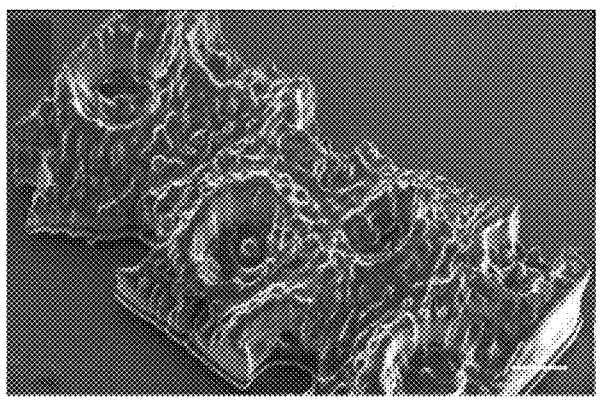
Figure 1D:
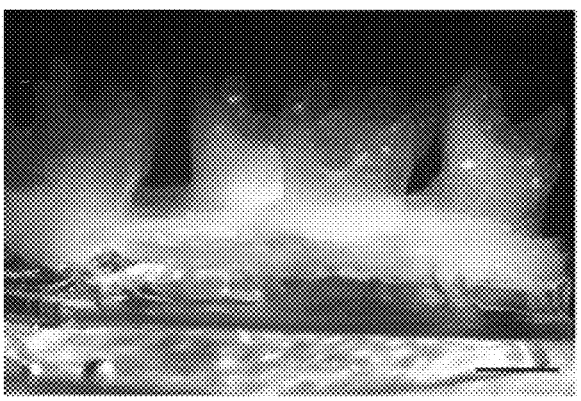

The bioprinting platform employs 3D printing to fabricate optically-tunable photosynthetic matter that mimics coral tissue and skeleton morphology with micron-scale precision (FIGS. 1A-1D). The inventive approach allows replication of any coral architecture, examples of which are shown in FIGS. 7A-7H, providing a variety of design solutions for augmenting light propagation. Fast-growing corals of the family Pocilloporidae are particularly relevant for studying light management. Despite high algal cell densities in their tissues ($1 \times 10^6$ cells per $cm^2$ surface area), the internal fluence rate distribution is homogenous, avoiding self-shading of the symbiotic microalgae. The photon distribution is mainly managed by the aragonite skeleton, where light leaks out of the skeleton and into coral tissue, supplying photons deep within the corallite. Additionally, light can enter the coral tissue more easily than it can escape, as low angle upwelling light is trapped by internal reflection due to refractive index mismatches between the coral tissue and the surrounding seawater. The inventive approach mimics these light management strategies to produce a bionic coral formed from sustainable polymers that are highly effective in enhancing microalgal light absorption and growth.

To precisely control the scattering properties of the bio-inspired artificial tissue and skeleton, a 2-step continuous light projection-based approach, described below, is employed for multilayer 3D bioprinting. Optimization of the printing approach involved balancing between several parameters including printability (resolution and mechanical support), cell survival, and optical performance. The artificial coral tissue constructs were fabricated with a novel bio-ink solution, in which the symbiotic microalgae (*Symbiodinium* sp.) were mixed with a photopolymerizable gelatin-methacrylate (GelMA) hydrogel and cellulose-derived nanocrystals (CNC), the latter providing mechanical stability and allowed tuning of the tissue's scattering properties. Similarly, the artificial skeleton was 3D printed with a polyethylene glycol diacrylate-based polymer (PEGDA) doped with CNC.

Key goals to be achieved in material design were: 1) high microalgal cell viability and growth; 2) microscale printing resolution; and 3) optimization of light scattering and biomechanical parameters including material stiffness, porosity and molecular diffusion. The photo-induced, free radical polymerization mechanism underlying the 3D printing technique allowed precise control the mechanical properties via modulating the crosslinking density of the polymerized parts. Any material and fabrication parameters (e.g., light intensity, exposure time, photoinitiator concentration, material composition) that affect the crosslinking density can be employed to tune the mechanical properties of the printed parts. Initially, different concentrations of prepolymer and photoinitiator combinations were evaluated, including glycidal methacrylate-hyaluronic acid (GM-HA), gelatin methacrylate (GelMA), polyethylene glycol diacrylate (PEGDA), and poly(lactic acid), together with the photoinitiators Irgacure 651 and lithium phenyl-2,4,6 trimethylbenzoylphosphinate (LAP). Cell viability and growth were higher in GelMA compared to PEGDA (data not shown), possibly due to favorable diffusion characteristics of GelMA due to its highly porous microstructure, while PEGDA has stronger mechanical stiffness. To take advantage of the properties of both materials, we combined PEGDA with GelMA to make a mechanically robust and tunable hydrogel. GelMA was initially doped with graphene oxide, which enhanced mechanical stability but limited light penetration and cell growth. To avoid UV damage to the algae, photopolymerization is preferably induced using light within the visible spectra. While the 3D printing steps described herein used 405 nm light, the use of visible light for initiating photopolymerization is widely reported in the literature and selection of alternative wavelengths would be within the level of skill in the art.

Figure 8A:
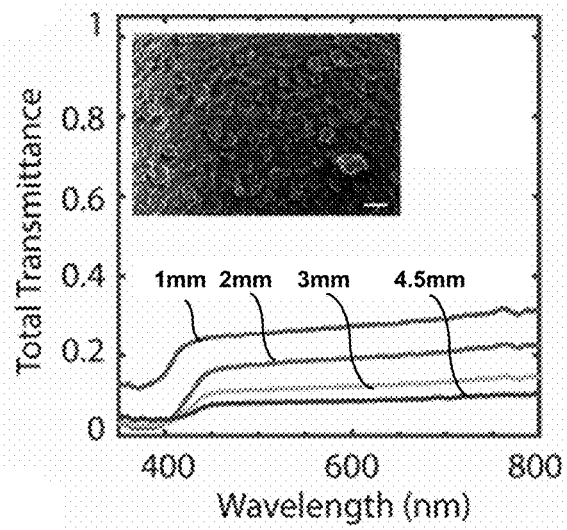
FIGS. 8A-8F are plots of optical characterization of 3D printed constructs, where
Figure 8B:
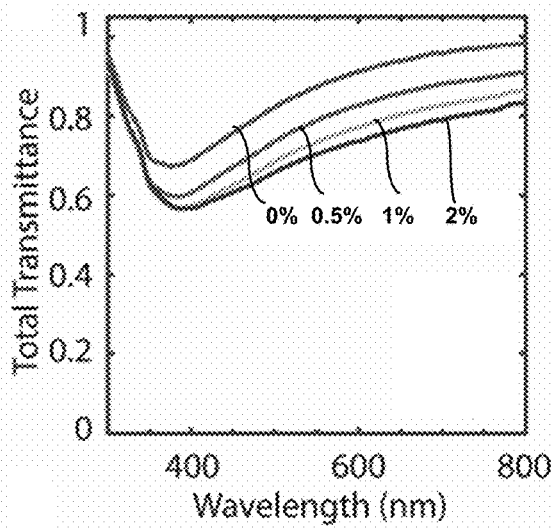
Figure 8C:
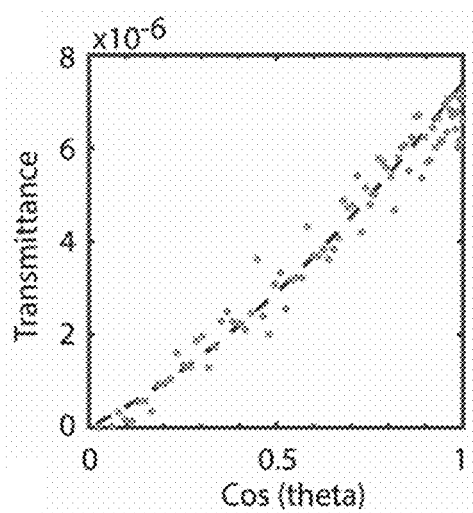

To optimize light scattering, we first mixed the hydrogel with different concentrations of $SiO_2$ particles (Sigma-Aldrich, USA) that were in a size range (about 10 μm) to induce broadband white light scattering with high scattering efficiency. However, when mixed into the hydrogels, the $SiO_2$ particle showed a vertical concentration gradient related to the particle sinking speed in the gel. Instead, we used cellulose nanocrystals (CNCs), which exhibit suitable light scattering, mechanical properties and low mass density. CNCs can be considered as rod-shaped colloidal particles (typical length of 150 nm and a width of a few nm in diameter), which have high refractive index (about 1.55 in the visible range). CNCs have been the subject of increasing interest in photonics due to their colloidal behavior and ability to self-assemble into cholesteric optical films. In the 3D bioprinted coral skeleton samples that contain 7% CNCs (w/v), we found that CNCs aggregated to form microparticles with a size range of 1-10 μm. These aggregated microparticles are highly efficient white light scatterers (FIG. 8A). In contrast, the 3D bioprinted bionic coral tissue constructs contained only 0.1% CNCs (w/v), and we did not observe any aggregated CNC microparticles.

The printing polymer (bio-ink) for the bionic coral tissue constructs was made up of final concentrations of: *Marinichlorella kaistiae* KAS603 ($1 \times 10^6$ cells $mL^{-1}$), GelMA (5% w/v), LAP (0.2% w/v), food dye (1% v/v), PEGDA (6000 Da; 0.5% w/v), CNC (0.1% w/v), and artificial seawater (ASW; 93.2%). The food dye (yellow, from Wilton® Candy Colors) was added to limit the penetration of polymerization-inducing light into the bio-ink. This leads to higher light absorption relative to scattering and enhanced the spatial resolution of the printing. The food dye is non-toxic and diffuses out after 24 hr.

To create a digital mask of natural coral surfaces, a spectral-domain (SD) optical coherence tomography (OCT) system (Ganymede II, Thorlabs GmbH, Dachau, Germany) was used to image living corals. FIGS. 7A-7H are USB camera images and respective optical coherence tomography scans of natural corals (FIGS. 7A, 7C, 7E and 7G) and 3D printed replica (FIGS. 7B, 7D, 7F and 5H). Skeletal 3D printed constructs were imaged with an environmental SEM, while 3D printed tissue constructs were photographed with a microscope camera. Scale bar=1 mm (7A, 7B, 7D, 7E, 7G) and 500 µm (7C, 7F, 7H).

The OCT system was equipped with a superluminescent diode (centered at 930 nm) and an objective lens (effective focal length=36 mm) (LSM03; Thorlabs GmbH, Dachau, Germany) yielding a z-resolution of 4.5 µm and a x-y resolution of 8 µm in water. The imaged coral species (*Pavona cactus, Stylophora pistillata, Pocillopora damicornis, Favites flexuosa*) were maintained at the Centre Scientifique de Monaco, and corals were imaged under controlled flow and irradiance conditions. For OCT imaging of bare coral skeletons, the living tissue was air brushed off the skeleton. The skeleton was carefully cleaned before imaging the bare skeleton in water. OCT scanning was performed as described previously.

OCT data was extracted as multiple 16-bit TIFF image stacks and imported into MATLAB® (Matlab 2018a). Image acquisition noise was removed via 3D median filtering. Segmentation of the outer tissue or skeletal surface was done via multilevel image thresholding using Otsu's method on each image of every TIFF stack. The binary files were exported as x,y,z point clouds and converted to a stl file format, which could be sliced into 2D image sequences for bioprinting. If the generated stl files showed holes in the surface mesh, these holes were manually filled using Meshlab (Meshlab 2016).

The bionic coral design was developed as an optimization between algal growth rates, optical performance and the outcome of optical models (FIGS. 2A-2D, 3A-C; 4A-4C; FIGS. 8A-8F, FIG. 9). The final bionic coral was designed in CAD software (Autodesk 3ds Max, Autodesk, Inc, USA) and was then sliced into hundreds of digital patterns with a custom-written MATLAB program. The digital patterns were uploaded to a digital micromirror device (DMD) in sequential order and used to selectively expose the prepolymer solution for continuous printing. A 405-nm visible LED light panel was used for photopolymerization. A digital micromirror device (DMD) consisting of 4 million micromirrors modulated the digital mask projected onto the prepolymer solution for microscale photopolymerization.

Figure 11:
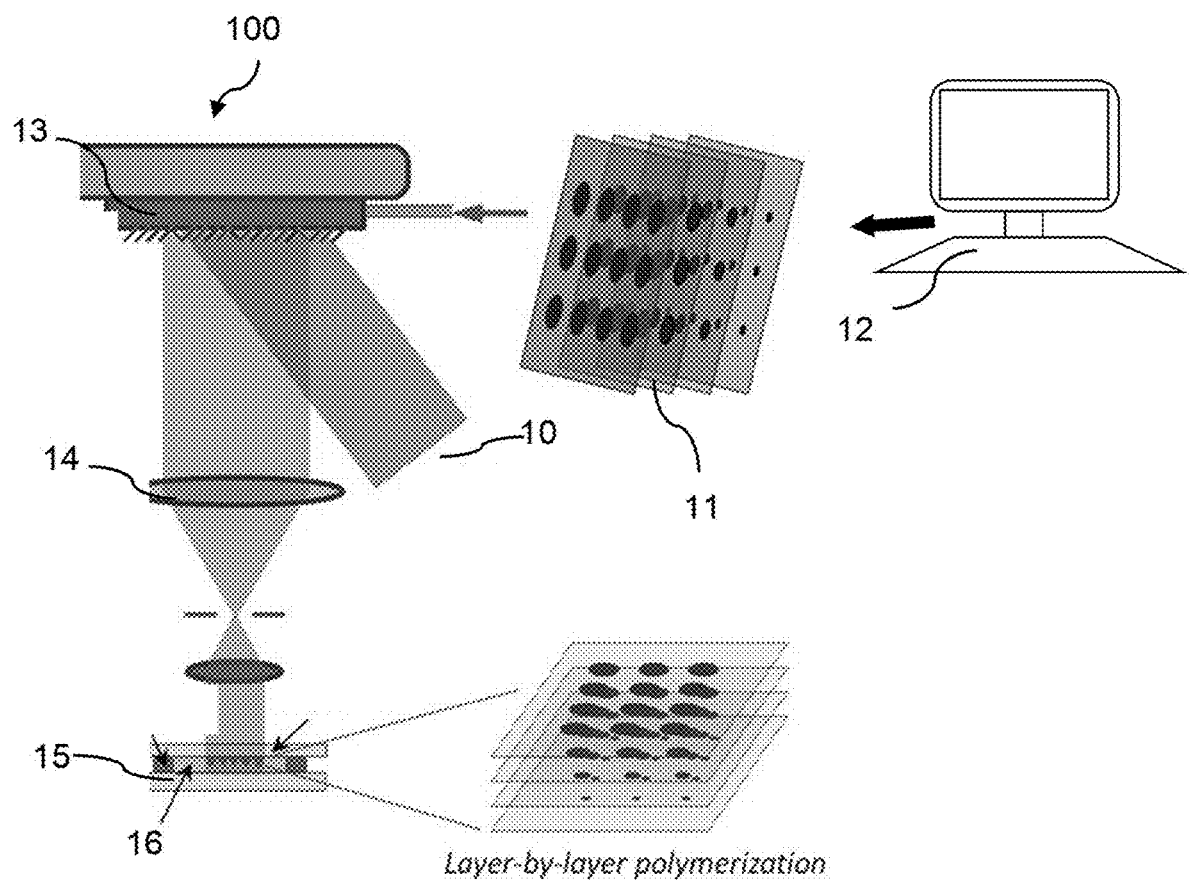
FIG. 11 is a schematic diagram of an embodiment of the 3D printing platform for use in fabrication of the bionic corals.

The basic components of a 3D printing platform 100 for use in an exemplary embodiment of the invention are illustrated in FIG. 11: a light source 10, a computer controller/processor 12, which performs sliced image-flow generation, i.e., "virtual masks" 11, and system synchronization, a digital micromirror device (DMD) chip 13 for optical pattern generation, a projection optics assembly 14, and an multi-axis stage 15 for sample position control. The DMD chip 13 modulates the light and projects the digital pattern generated via computer 12 based on a custom-designed computer-aided design (CAD) model onto the photopolymer solution. The optical pattern is projected through optical lenses 14 and onto the photosensitive biomaterial 16 to fabricate a 3D scaffold. Complex 3D structures are fabricated through a continuous, layer-by-layer polymerization process that is synchronically controlled using a motorized multi-axis stage 15.

An appropriate light source 10 for use in the 3D printing system can be selected from different sources including a laser (CW or pulsed), arc lamp, and an LED source, which may include an array of LEDs emitting at a single wavelength or across a range of wavelengths. The light source 10 may include controllable parameters, responsive to the computer controller/processor 12, including intensity, iris, aperture, exposure time, shutter, and wavelength. Selection of appropriate operating parameters will depend on the materials used and the desired characteristics of the scaffold and will be within the level of skill in the art.

The continuous movement of the DMD was synchronized with the projected digital mask to create smooth 3D constructs that are rapidly fabricated without interfacial artifacts. To print the bionic coral, a 2-step printing approach was developed. In the first step, the PEGDA bio-ink was used to print the coral inspired skeleton. The resulting hydrogel was attached to a glass slide surface, washed with DI water and then dried with an air gun. In the second step, the algal cell-containing bio-ink for tissue printing was then injected with a pipette into the skeletal cavities in order to fill the air gaps. The gap-filled skeletal print was repositioned at the identical spot on the bioprinter, and the bionic coral tissue mask was loaded. The z-stage was moved such that the surface of the skeletal print touched the glass surface of the bioprinter.

Figures 2A, 2B:
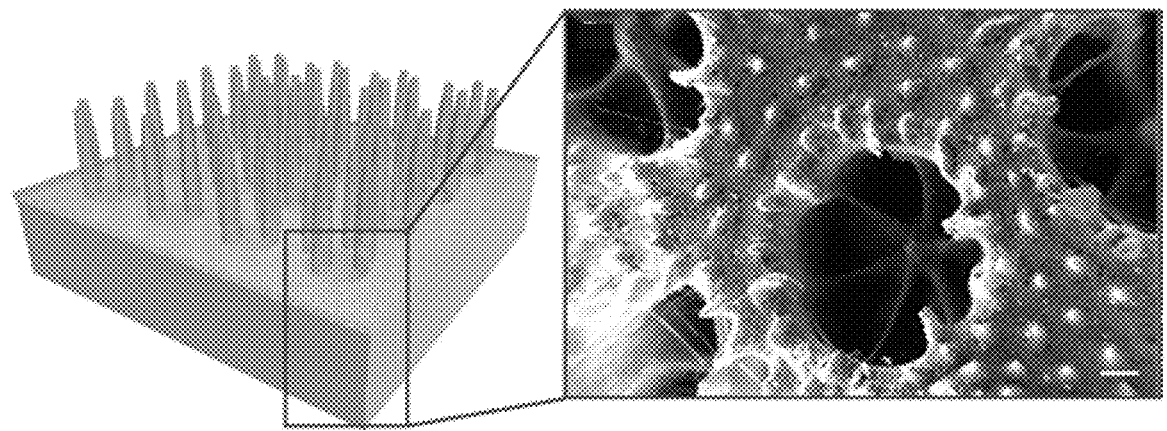
FIGS. 2A-2D illustrate optical properties of 3D printed bionic coral tissue and skeleton, where
Figures 2C, 2D:
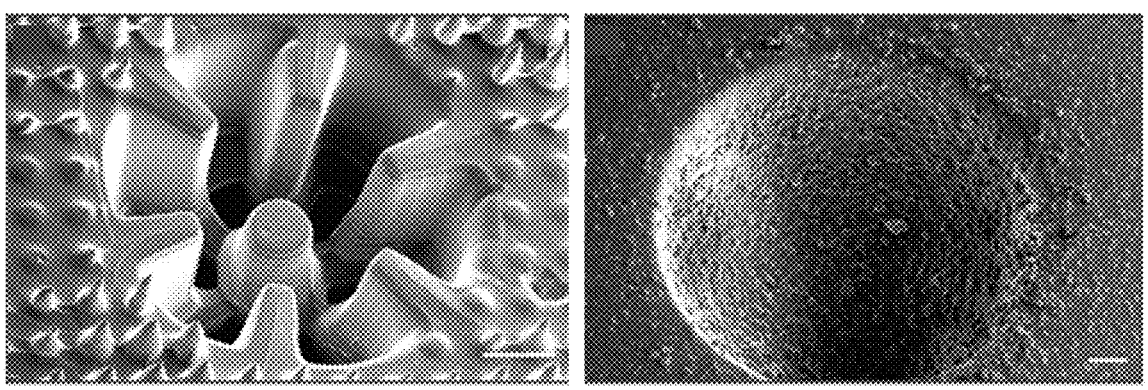
Figure 4A:
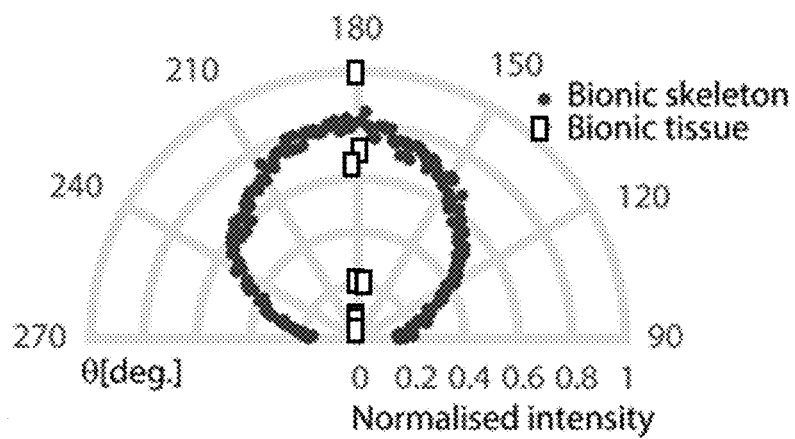
FIG. 4A plots the angular distribution of forward scattered light ($\theta=270°$-$90°$) at 550 nm shown as normalized transmittance.

Based on optimization via experiments and optical simulations (FIGS. 2A-2D, 3A-3C and 4A-4C), the functional unit of the artificial skeleton was an abiotic cup structure, shaped like the inorganic calcium carbonate corallite (1 mm in diameter and depth) and tuned to redistribute photons via broadband diffuse light scattering (scattering mean free path=3 mm between 450-650 nm) and a near isotropic angular distribution of scattered light (FIG. 4A, FIGS. 8A-8F), similar to the optical properties of the skeleton of fast-growing intact corals. The coral-inspired tissue had cylinder-like projections (200 µm wide and 1 mm long) radially arranged along the periphery of the corallites mimicking coral tentacles, which serve to enhance surface area exposed to light (FIG. 2A). We designed the bionic coral tissue to have a forward scattering cone (FIG. 4A), which enabled light to reach the diffusely backscattering skeleton (FIG. 2A).

Figure 4B:
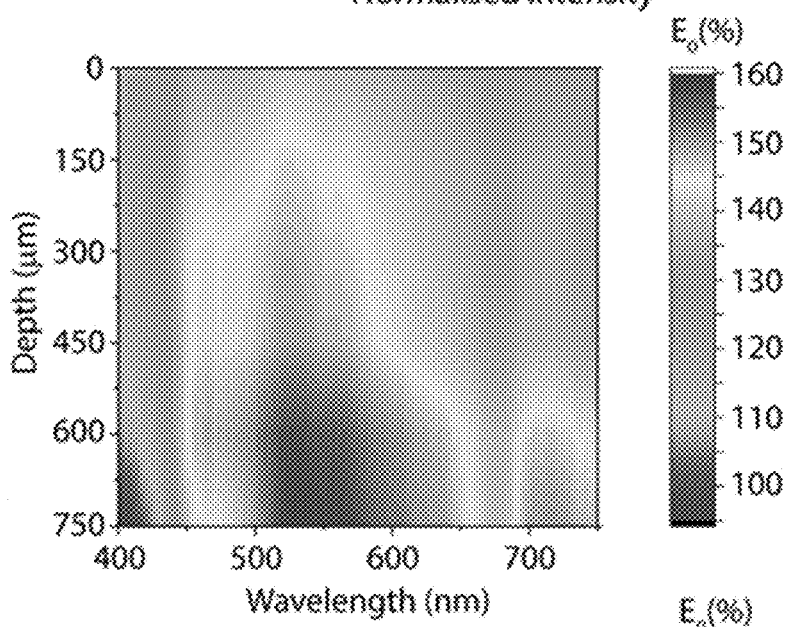
FIGS. 4B and 4C show microprobe-based fluence rate measurements ($E_0$ in % of incident irradiance) for the bionic coral and a flat slab of GelMA, respectively, both with a microalgal density of $5.0\times106$ cells $mL^{-1}$.
Figure 4C:
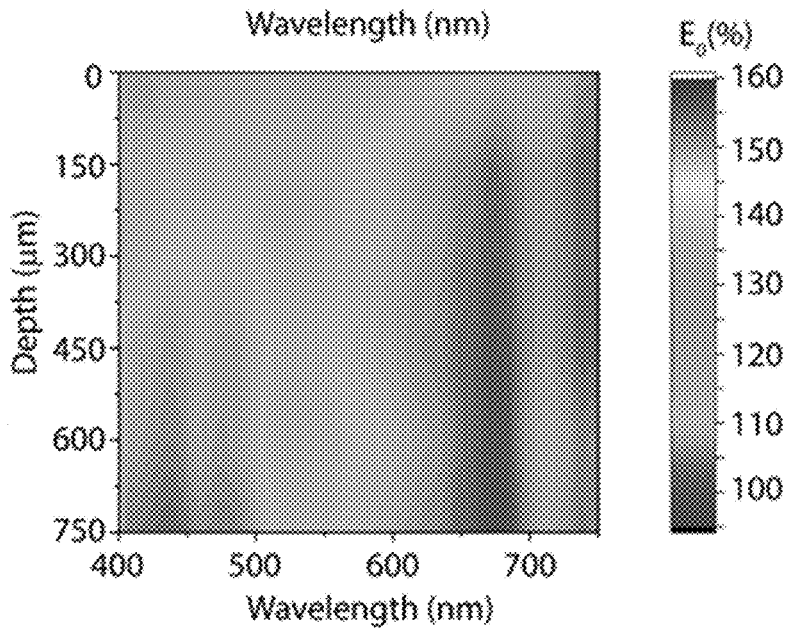
Figure 9:
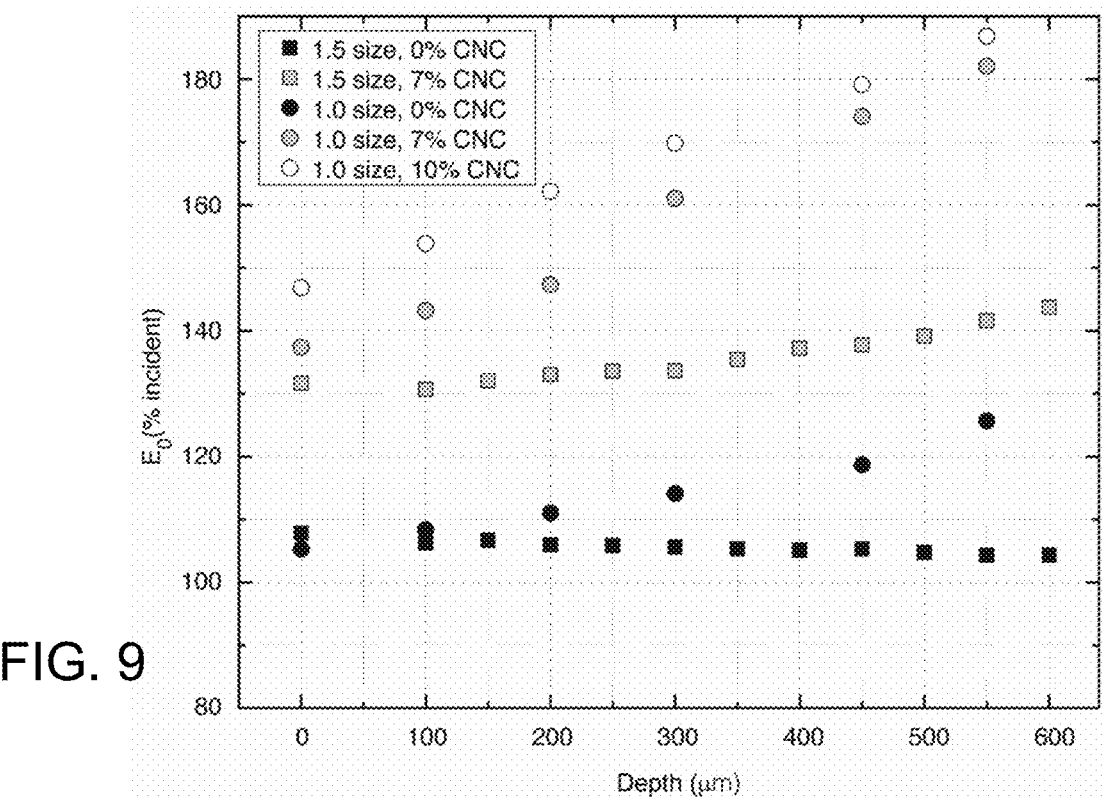
FIG. 9 plots the impact of CNC doping and corallite cup size on fluence rate ($E_0$) attenuation. Measurements were performed for different CNC concentrations (0-10%) using the original corallite cup size (maximal width=1 mm) and a 1.5-fold enhanced size. $E_0$ (fluence rate) was normalized to the vertically incident downwelling irradiance $E_d$.

The bionic coral disclosed herein increased the photon residence time as light travelled through the algal culture (FIG. 3A), consequently enhancing the chance of light absorption for photosynthesis by algae located deeper within the structure. As photons travelled through the bionic skeleton, they were redirected into the photosynthetic tissue. The contribution of the scattered light increased with depth, effectively delivering light to the deepest part of the bionic coral (FIG. 4B, FIG. 9). This photon augmentation strategy led to a steady increase of irradiance with tissue depth, which counter balanced the exponential light attenuation by photopigment absorption (FIG. 3C). Compared to a flat slab of biopolymer (GelMA) with the same microalgal density ($5.0 \times 10^6$ cells/mL), the fluence rate (for 600 nm light) measured in the photosynthetic layer of the bionic coral was more than 1.5-fold enhanced at 750 µm depth due to the optimised scattering properties of the bionic coral tissue and skeleton, as shown by FIGS. 4B and 4C.

Three microalgal species were chosen for inclusion in 3D bioprinted polymers: dinoflagellates belonging to the genus *Symbiodinium*, the green alga *Marinichlorella kaistiae*, and the diatom *Thalassiosira pseudonana*. Stock cultures of *Symbiodinium* strains A08 and A01 (obtained from Mary Coffroth, University of Buffalo) were cultured in F/2 medium in a 12 h/12 h light:dark cycle under an irradiance (400-700 nm) of 200 µmol photons $m^{-2}$ $s^{-1}$. Wild type *M. kaistiae* strain KAS603[19] were obtained from Kuehnle AgroSystems, Inc. (Hawaii) and were cultivated at 25° C. in artificial seawater (ASW) medium[30] under continuous light from cool white fluorescent lamps (80 µmol photons $m^{-2}$ $s^{-1}$). Stock cultures were harvested during exponential growth phase for use in bioprinting.

Figure 5A:
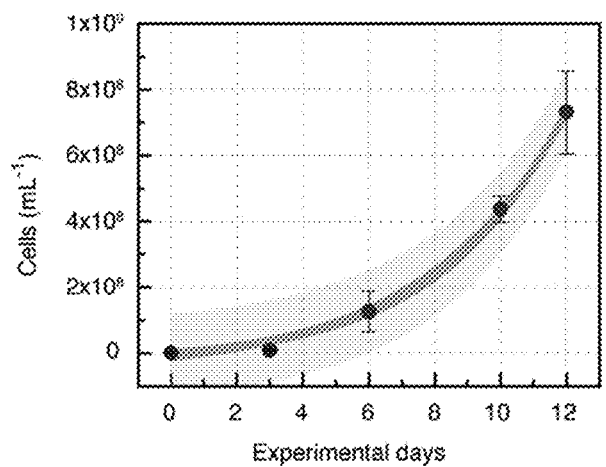
FIGS. 5A-5D provide the results of performance testing of 3D printed bionic coral, where FIG. 5A plots growth of *M. kaistiae* KAS603 in bionic coral.
Figure 5B:
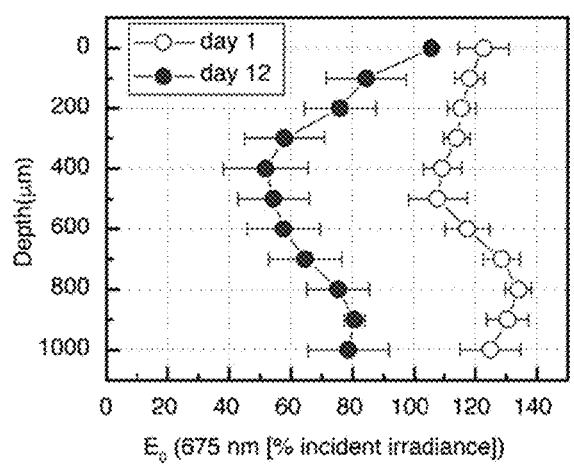
Figure 5C:
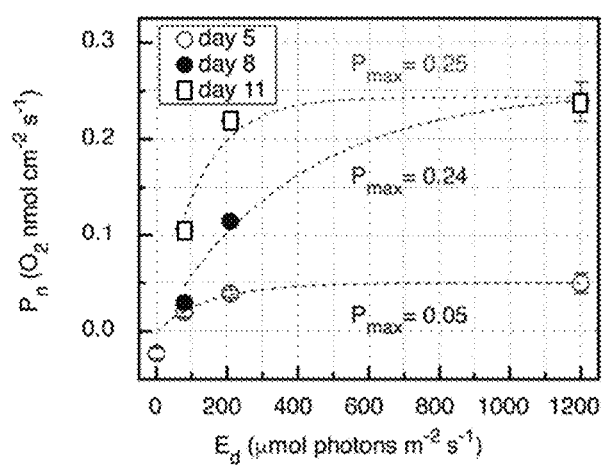
Figure 5D:
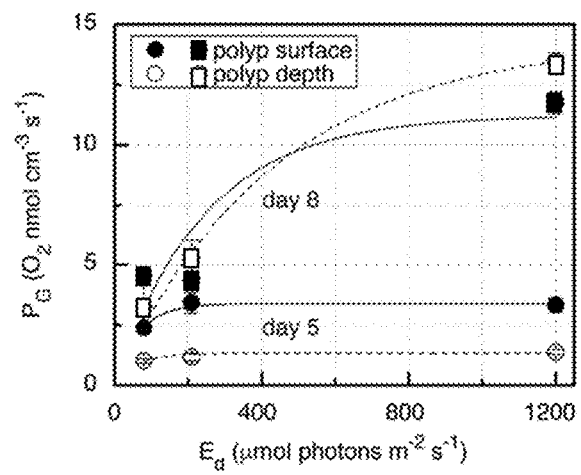
Figure 7A:
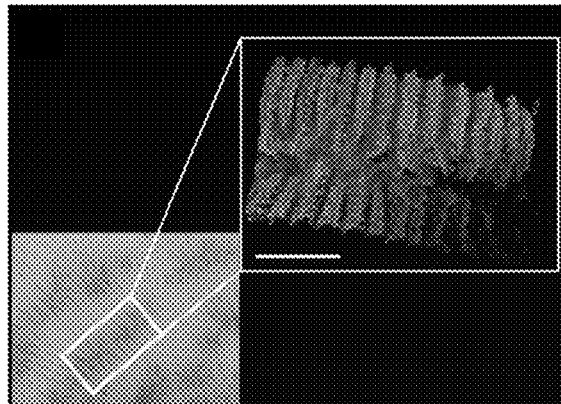
Figure 7B:
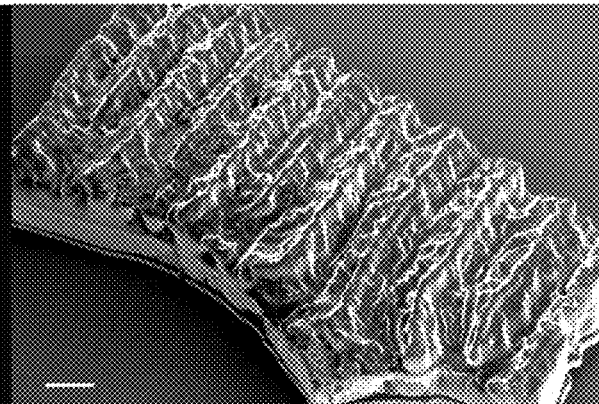
Figure 7C:
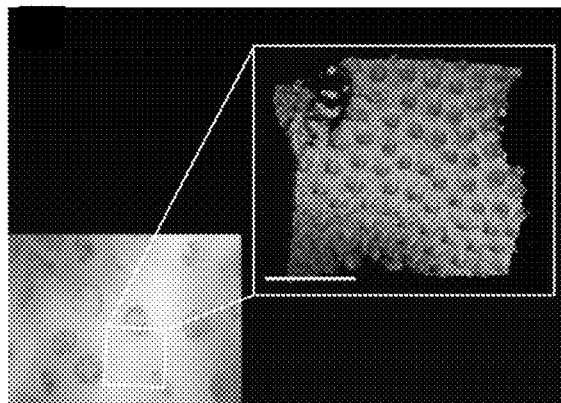
Figure 7D:
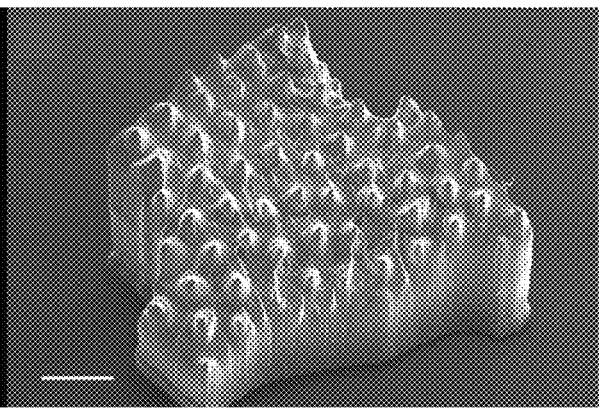
Figure 10:
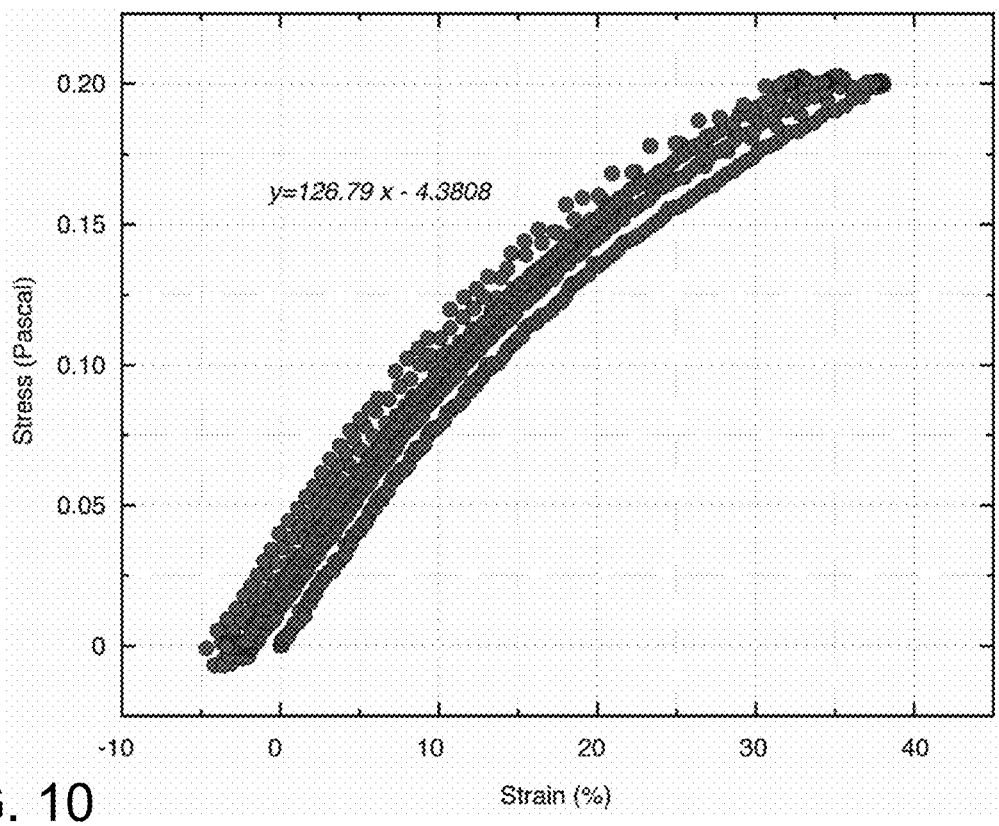
FIG. 10 shows the stress-strain analysis of coral-inspired bionic tissue. Replicate measurements of 6 bionic tissues were performed. The average elastic modulus was E=4.3 kPa.

In order to evaluate the growth of a commercially-relevant microalgal species in the inventive bionic coral, we cultured the green alga *Marinichlorella kaistiae* KAS603, the results of which are plotted in FIGS. 5A-5D. Although the main focus of the inventive bionic coral design was to improve light management, it also allows for growing microalgae without the need for energy-intensive turbulent flow and mixing, which is otherwise required for optimal nutrient and light delivery in photobioreactors. This is achieved by the combination of the bionic tissue and skeleton replica morphology, the tissue mechanical properties (average Young's modulus, E=4.3 kPa, FIG. 10) and its porosity (pore size diameter=5-40 μm). We grew *M. kaistiae* KAS603 under no-flow conditions and low incident irradiance ($E_d$=80 μmol photons $m^{-2}$ $s^{-1}$) in our bionic coral, where it reached algal cell densities of >8×10$^8$ cells mL$^{-1}$ by day 12. In the FIG. 5A plot of *M. kaistiae* KAS603 growth in bionic coral, data are means (±SEM, n=3-6 bionic coral prints), and darker and lighter shaded areas indicate 95% confidence and prediction intervals, respectively. This is about one order of magnitude higher than the maximal cell densities reported for this algal species when grown in flasks under continuous stirring. Despite such high algal cell densities, irradiance did not limit growth at depth, and about 80% of the incident irradiance remained at 1 mm depth within the bionic coral tissue construct. FIG. 5B plots vertical attenuation of fluence rate ($E_0$ at 675 nm) at the beginning (day 1) and end of the performance test (day 12). Measurements were performed with $O_2$ microsensors at the center of the corallite cup surface (closed symbols/solid lines) and at a vertical depth of 300 μm (open symbols/dashed lines). Symbols are means (±SEM, n=3-6 bionic coral prints), lines are curve fits.). In comparison, biofilm-based photobioreactors show exponential light attenuation characterized by a virtual depletion of irradiance within 200-300 μm of the biofilm thickness. We observed that *M. kaistiae* KAS603 grew in the bionic tissue as dense aggregates (sphericity 0.75±0.09 SD, diameter=30-50 μm; FIGS. 6A-6C). Algal photosynthesis within the tissue construct yielded a net photosynthetic $O_2$ production of 0.25 nmol $O_2$ $cm^{-2}$ $s^{-1}$ at the polyp tissue surface. FIG. 5C plots net photosynthetic rates at day 5, 8 and 11, where lines represent curve fits. Gross photosynthesis within 8-day old bionic coral polyps was enhanced at a depth of 300 μm compared to gross photosynthesis rates measured at the surface of the bionic coral tissue. FIG. 5D plots gross photosynthetic rates at day 5 (dot) and day 8 (rectangle) for the polyp surface (solid) and the polyp depth (open).

Bionic corals harboring *Symbiodinium* sp. or *M. kaistiae* KAS603 were cultured under similar conditions as the respective algal stock cultures. Prior to bioprinting, the bio-ink for printing bionic coral tissue constructs was inoculated with cell densities of 1×10$^6$ cells mL$^{-1}$ from exponentially growing cultures. We performed growth experiments with 35 bionic corals harboring *M. kaistiae* KAS603. The bionic corals were transferred to 6-well plates filled with 3 mL of ASW medium containing broadband antibiotics (penicillin/streptomycin, Gibco) at a concentration of 1:1000. All prints were illuminated with an incident downwelling irradiance (400-700 nm) of 80 μmol photons $m^{-2}$ $s^{-1}$ provided by LED light panels (AL-H36DS, Ray2, Finnex) emitting white light. The prints were grown without mixing at 25° C. The ambient growth medium was replenished at day 5 and day 10. Degradation of GelMA-based tissue occurred after about 10-14 days when bacterial abundance was kept low via antibiotic treatment. Such degradation kinetics can be advantageous for more easy harvesting of the highly concentrated microalgae that are contained within the hard PEGDA-based skeleton. In order to obtain values of algal productivity comparable with previous studies we produced an additional subset of bionic corals in slab geometry (FIG. 14, discussed below). For these experiments, bionic corals were illuminated with an incident irradiance of 150 μmol photons $m^{-2}$ $s^{-1}$ and supplied with filtered air supplied by an air pump.

Figure 8D:
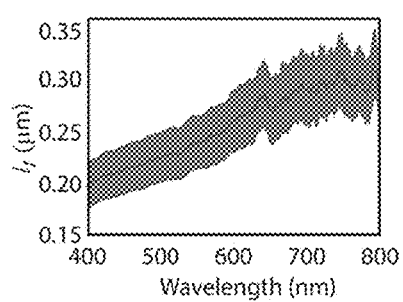
Figure 8E:
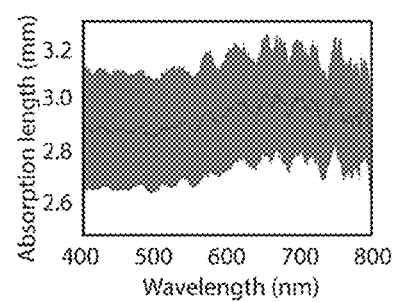
Figure 8F:
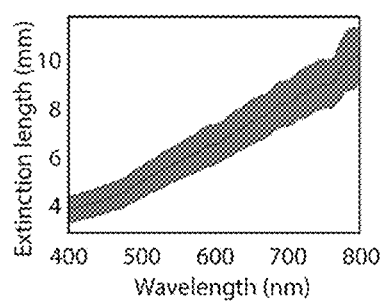

The angular distribution of transmitted light was measured using an optical goniometer. The samples were illuminated using a Xenon lamp (Ocean Optics, HPX-2000) coupled into an optical fiber (Thorlabs FC-UV100-2-SR). The illumination angle was fixed at normal incidence and the angular distribution of intensity was acquired by rotating the detector arm with an angular resolution of 1°. To detect the signal, a 600 μm core optical glass fiber (Thorlabs FC-UV600-2-SR) connected to a spectrometer (Avantes HS2048) was used. To characterize the optical properties, the total transmitted light was measured for different sample thicknesses using an integrating sphere. The samples were illuminated by a Xenon lamp (Ocean Optics, HPX-2000) coupled into an optical fiber (Thorlabs FC-UV100-2-SR), and the transmitted light was collected with an integrating sphere (Labsphere Inc.) connected to a spectrometer (Avantes HS2048). In the case of the skeleton-inspired samples, where the light is scattered multiple times before being transmitted, the light transport can be described by the so-called diffusion approximation. In this regime, the analytical expression, which describes how the total transmission (T) scales with the thickness (L) for a slab geometry, is given as:

$$T = \frac{1}{l_a} \frac{\sinh\left(\frac{z_e \times l_t}{l_a}\right)\sinh\left(\frac{z_e \times l_t}{l_a}\right)}{\sinh\left(\frac{L + z_e \times l_t}{l_a}\right)} \quad (1)$$

where $l_a$, $l_t$ and $z_e$ are the absorption length, the transport mean free path and the extrapolation length, respectively. Here, $z_e$ quantifies the effect of internal reflections at the interfaces of the sample in the estimation of $l_a$ and $l_t$. We quantified $z_e$ by measuring the angular distribution of transmitted light, P(μ), which is related to $z_e$ by the following equation:

$$P(\mu) = \mu \frac{z_e + \mu}{\frac{1}{2}z_e + \frac{1}{3}} \quad (2)$$

where μ is the cosine of the transmission angle with respect to the incident ballistic beam. The theoretical fit is shown in Figure S2C and led to a value of $z_e$=(1.32±0.12). Once the extrapolation length was estimated, the values of $l_a$ and $l_t$ could be calculated with Eq. (1) (FIGS. 8D, 8E). This was done with an iteration procedure to check the stability of the fit, as described previously. In the bionic coral tissue, the scattering strength of the material is too low and the diffusion approximation cannot be applied. In this regime, the extinction coefficient can be estimated using the Beer-Lambert law (FIG. 8F).

The refractive index (n) of the bioprinted bionic coral tissue was determined with the optical goniometer to characterize the Brewster angle ($\theta_B$). A half circle of the material was printed with a diameter of 2 cm and a thickness of z=5 mm. The Brewster angle was calculated according to Snell's law:

$$n = \frac{\sin(\theta_i)}{\sin(\theta_r)} = \frac{\sin(\theta_i)}{\sin(\theta_{90-i})} = \tan(\theta_i) \quad (3)$$

and Brewster's law:

$$\theta_B = \arctan\frac{n_2}{n_1} \quad (4)$$

where $\theta_i$ is the angle of incidence, and $\theta_r$ is the angle of refraction. $n_1$ and $n_2$ are the refractive indices of the medium and the surrounding medium, respectively. For the coral-inspired tissue $\theta_B$ ranged between 54.0° and 55.0° yielding a refractive index of n=1.37-1.40.

Tetrahedral meshes were generated via Delaunay triangulation using the MATLAB based program Iso2mesh that calls cgalmesh. Meshing was performed with different mesh properties varying maximal tetrahedral element volume and Delaunay sphere size in order to optimize simulation efficiency. Settings were optimized for a Delaunay sphere of 1 (10 µm) and a tetrahedral element volume of 5 (50 µm). Generated tetrahedral meshes were used as source architecture for a mesh-based 3D Monte-Carlo light transport simulation (mmclab). The model uses the generated tetrahedral mesh and calculates photon propagation based on the inherent optical parameters, the absorption coefficient $\mu_a$ [mm$^{-1}$], the scattering coefficient $\mu_s$ [mm$^{-1}$], the anisotropy of scattering g [dimensionless] and the refractive index n [dimensionless]. The optical parameters were extracted via integrating sphere measurements (see above) and were used to calculate time-of-flight photon propagation in the bionic coral. The probe illumination was a collimated point source with varying source positions.

To evaluate the mechanical properties of bionic tissue, the Young's modulus of the bionic coral tissue was evaluated with a microscale mechanical strength tester (Microsquisher, CellScale). Each sample was preconditioned by compressing at 4 µm s$^{-1}$ to remove hysteresis caused by internal friction. The compression test was conducted at 10% strain with a 2 µm s$^{-1}$ strain rate. Cylindrical constructs were 3D printed using the same bio-ink as used to print bionic coral tissue. The Young's modulus was calculated from the linear region of the stress-strain curve. Three samples were tested, and each sample was compressed three times.

Cell density was determined at the beginning of the experiment (day 0) and then at day 3, day 6, day 10 and day 12 of the growth experiments. To determine cell density, the construct was removed from the growth medium, and any remaining solution attached to the construct was removed with a Kimwipe. Each construct was transferred to a 1.5 mL microfuge tube and the hydrogel was dissolved via adding 600 µL trypsin solution (0.25% Trypsin/EDTA) under incubation at 37° C. for 40 min. This procedure removed the microalgal cells from the matrix allowing for cell counting via a haemocytometer. The accuracy of this approach was verified by printing known cell densities (from liquid culture) and comparing it to the trypsin-based estimates yielding a deviation of <3%. However, the matrix itself is biocompatible and non-toxic and does not need to be removed to harvest algal biomass. Additionally, as the harvesting of lipids and bioproducts (e.g., pigments) relies on solvents that can diffuse into the scaffold, matrix degradation is not required for extraction.

To compare our cell density estimates with ash free dry weight (AFDW) of algal cell biomass [g], which is a commonly used metric in biofuels research, we determined AFDW using methods described previously. AFDW was on average 3.47×10$^{-11}$ g cell$^{-1}$ (±4.6×10$^{-13}$ SE). The maximal growth rate was obtained from readings of Day 10 and Day 12, yielding 1.47×10$^{11}$ cells L$^{-1}$ day$^{-1}$ or 5.1 g L$^{-1}$ day$^{-1}$. The aerial productivity was extrapolated to g m$^{-2}$ day$^{-1}$ by accounting for the area occupied by one bionic coral (6 mm in length and width) and the measured productivity per bionic coral.

Photosynthetic performance of the bionic corals was characterized using Clark-type $O_2$ microsensors (tip size=25 µm, response time <0.2 s; OX-25 FAST, Unisense, Aarhus, Denmark). Net photosynthesis was measured via linear $O_2$ profiles measured with $O_2$ microsensors from the surface into the overlying diffusive boundary layer. The sensors were operated via a motorized micromanipulator (Pyroscience, Germany). The diffusive $O_2$ flux was calculated via Fick's first law of diffusion for a water temperature=25° C. and salinity=30 using a molecular diffusion coefficient for $O_2$=2.255×10$^{-5}$ cm$^2$ s$^{-1}$. Gross photosynthesis was estimated via the light-dark shift method. A flow chamber set-up provided slow laminar flow (flow rate=0.5 cm s$^{-1}$) and a fiber-optic halogen lamp (Schott KL2500, Schott, Germany) provided white light at defined levels of incident irradiance (400-700 nm) (0, 110, 220, and 1200 µmol photons m$^{-2}$ s$^{-1}$). Photosynthesis-irradiance curves were fitted to an exponential function[42].

The fluence rate (=scalar irradiance), $E_0$, within the bionic coral was measured using fiber-optic scalar irradiance microsensors with a tip size of 60-80 µm and an isotropic angular response to incident light of ±5% (Zenzor, Denmark). Fluence rate measurements were performed through the tissue at a vertical step size of 100 µm using an automated microsensor profiler set-up as described previously. Depth profiles were measured from the planar tissue surface (i.e. areas distant from the tentacles) into the center of the bionic corallite. Fluence rate was normalized to the incident downwelling irradiance, $E_d$, measured with the scalar irradiance sensor placed over a black light well at identical distance and placement in the light field as the surface of bioprinted constructs.

SEM images were taken with a Zeiss Sigma 500 scanning electron microscope. Samples were prepared in two different ways. To image the bionic coral skeleton made of PEGDA, samples were dried at room temperature and sputter coated with iridium (Emitech K575X Sputter Coater). To image the bionic coral tissue made of GelMA, samples were snap frozen with liquid nitrogen, and were then lyophilized in a freeze dryer (Freezone, Labonco) for 3 days. The overall shape could not be maintained, but microscale structures (such as micropores of GelMA) were well preserved. The samples were sputter coated with iridium (Emitech K575X Sputter Coater) prior to imaging on the SEM.

To characterize microalgal aggregate size and distribution in 3D, a confocal laser scan microscope was used (Nikon Eclipse TE-2000U). Bionic corals were placed on a cover glass and imaged from below with a 641 nm laser. Confocal stacks of chlorophyll a fluorescence were acquired using a pinhole size of 1.2 µm, a vertical step size for z-stacking=1 µm, and a x,y resolution of 0.6 µm. Particle segmentation and visualization of the data was performed in ImageJ and the NIS confocal elements software (Nikon). Particle segmentation was performed via manual thresholding of 229-4095 gray scale values, with a cleaning factor of 6× (this eliminates smaller particles that are not aggregates), hole filling and a smoothing factor of 2×. The segmented particles were analyzed for surface area, volume and particle density per volume.

Bionic corals enable microalgal cultivation with strongly reduced energy maintenance requirements, as they do not require water mixing and the fluence rate within the biomaterial is up to two-fold enhanced relative to the incident light source (FIGS. 4B, 4C). By comparing our developed bionic corals to various microalgal cultivation platforms, we conclude that no other cultivation system combines excellent light use efficiency with high productivity, low maintenance requirements, excellent water usage, and the ability for spatially controlled cell growth (FIGS. 12A-12C). While traditional systems use glass, excess water, and costly aeration, bionic corals consist of a hydrogel system with minimal water usage, optimized light propagation, and gas flux.

The table provided in FIG. 13 summarizes performance results comparing the inventive bionic coral against a variety of cultivation platforms as reported in the literature, including open pond, stirred flask, flat panel, vertical column, horizontal tubular, biofilm twin layer, polystyrene foam, rotating algal disk and algal turf scrubber. We compared liquid cultivation platforms and state of the art biofilm-based systems. Light use efficiency was calculated as gram algal biomass (ash free dry weight from the maximum specific growth rate or the maximum reported harvested biomass) per incident irradiance in mol photons of photosynthetically active radiation (400-700 nm) $m^{-2} d^{-1}$ (see [10]). Areal density describes the highest reported densities of algal biomass (AFDW) per $m^{-2}$ of exposed planar surface area. Water usage describes the amount of water needed accounting for both cultivation medium and dewatering processes. Maintenance accounts for the combined labor needed to operate the system. The bionic coral data stems from two different experimental set-ups. Enhanced productivity and light use efficiency were achieved using additional aeration and an incident light intensity of 150 μmol photons $m^{-2} s^{-1}$.

The high spatial efficiency of the bionic coral system is thus particularly suitable for the design of compact photobioreactors for algal growth in dense urban areas, or as life support systems for space travel. Moreover, bionic corals allow investigation of the cellular activity of specific *Symbiodinium* strains, while mimicking the optical and mechanical microenvironment of different coral species, thus providing an important tool for advancing animal-algal symbiosis and coral bleaching research. Bionic corals have applications from biological studies to commercial technologies for efficient photon augmentation for sustainable bioenergy and bioproduct generation.

REFERENCES

1. Hatcher, B. G. Coral reef primary productivity: a beggar's banquet. *Trends. Ecol. Evol.* 3, 106-111 (1988).
2. Brodersen, K. E., Lichtenberg, M., Ralph, P. J., Kühl, M., Wangpraseurt, D. Radiative energy budget reveals high photosynthetic efficiency in symbiont-bearing corals. *J. R. Soc. Interface* 11, 20130997 (2014).
3. Roth, M. S. The engine of the reef: photobiology of the coral-algal symbiosis. *Front. Microb.* 5, 422 (2014).
4. Wangpraseurt, D., Jacques, S. L., Petrie, T., Kühl, M. Monte Carlo modeling of photon propagation reveals highly scattering coral tissue. Front. *Plant Sci.* 7, 1404 (2016).
5. Enriquez, S., Mendez, E. R., Hoegh-Guldberg, O. Iglesias-Prieto, R. Key functional role of the optical properties of coral skeletons in coral ecology and evolution. *Proc. R. Soc.* B. 284, 20161667 (2017).
6. Wijffels, R. H., Barbosa, M. J. An outlook on microalgal biofuels. *Science* 329, 796-799 (2010).
7. Ooms, M. D., Dinh, C. T., Sargent, E. H., Sinton, D. Photon management for augmented photosynthesis. *Nat. Commun.* 7, 12699 (2016).
8. Sanchez, C., Arribart, H., Guille, M. M. G. Biomimetism and bioinspiration as tools for the design of innovative materials and systems. *Nat. Mater.* 4, 277 (2005).
9. Lode, A., et al., Green bioprinting: Fabrication of photosynthetic algae-laden hydrogel scaffolds for biotechnological and medical applications. *Eng. Life Sci.* 15, 177-183 (2015).
10. van Oppen, M. J., Oliver, J. K., Putnam, H. M., Gates, R. D., Building coral reef resilience through assisted evolution. *Proc. Natl. Acad. Sci. U.S.A.* 112, 2307-2313 (2015).
11. Wangpraseurt, D., et al., In vivo microscale measurements of light and photosynthesis during coral bleaching: evidence for the optical feedback loop? *Front. Microb.* 8, 59 (2017).
12. Marcelino, L. A., et al., Modulation of light-enhancement to symbiotic algae by light scattering in corals and evolutionary trends in bleaching. *PLoS ONE* 8, e61492 (2013).
13. Kühl, M., Cohen, Y., Dalsgaard, T., Jørgensen, B. B., Revsbech, N. P. Microenvironment and photosynthesis of zooxanthellae in scleractinian corals studied with microsensors for $O_2$, pH and light. *Mar. Ecol. Prog. Ser.* 117, 159-172 (1995).
14. Parker, R. M., et al., Hierarchical self-assembly of cellulose nanocrystals in a confined geometry. *ACS Nano* 10, 8443-8449 (2016).
15. Zhu W. et al., Direct 3D bioprinting of prevascularized tissue constructs with complex microarchitecture. *Biomaterials* 124, 106-115 (2017).
16. Murphy, S. V., Atala, A. 3D bioprinting of tissues and organs. *Nat. Biotechnol.* 32, 773 (2014).
17. Wangpraseurt, D., Wentzel, C., Jacques, S. L., Wagner, M., Kühl, M. In vivo imaging of coral tissue and skeleton with optical coherence tomography. *J. R. Soc. Interface* 14, 20161003 (2017).
18. Slade, R., Bauen, A. Micro-algae cultivation for biofuels: cost, energy balance, environmental impacts and future prospects. *Biomass Bioenergy* 53, 29-38 (2013).
19. Sanchez-Alvarez, E. L., Gonzalez-Ledezma, G., Prats, J. A. B. Stephano-Hornedo, J. L., Hildebrand, M. Evaluating *Marinichlorella kaistiae* KAS603 cell size variation, growth and TAG accumulation resulting from rapid adaptation to highly diverse trophic and salinity cultivation regimes. *Algal Res.* 25, 12-24 (2017).
20. Li, T. et al., Microscale profiling of photosynthesis-related variables in a highly productive biofilm photobioreactor. *Biotechnol. Bioeng.* 113, 1046-1055 (2016).
21. Brennan, L., Owende, P. Biofuels from microalgae—a review of technologies for production, processing, and extractions of biofuels and co-products. *Renew. Sust. Energ. Revi.* 14, 557-577 (2010).
22. Truby, R. L., & Lewis, J. A. Printing soft matter in three dimensions. *Nature* 540 (7633), 371.
23. Hendrickx, L., Mergeay, M. From the deep sea to the stars: human life support through minimal communities. *Curr. Opin. Microbiol.* 10, 231-237 (2007).

24. Liu, J., Hwang, H. H., Wang, P., Whang, G., Chen, S. Direct 3D-printing of cell-laden constructs in microfluidic architectures. *Lab Chip* 16, 1430-1438 (2016).
25. Kolesky, D. B. et al., 3D bioprinting of vascularized, heterogeneous cell-laden tissue constructs. *Adv. Mater.* 26, 3124-3130 (2014).
26. Guidetti, G., Atifi, S., Vignolini, S., Hamad, W. Y. Flexible photonic cellulose nanocrystal films. *Adv. Mater.* 28, 10042-10047 (2016).
27. Zhu, W., et al., Rapid continuous 3D printing of customizable peripheral nerve guidance conduits. *Mater. Today* 9, 951-959(2018).
28. Nichol, J. W., et al., Cell-laden microengineered gelatin methacrylate hydrogels. *Biomaterials* 31, 5536-5544 (2010).
29. Fairbanks, B. D., Schwartz, M. P., Bowman, C. N., Anseth, K. S. Photoinitiated polymerization of PEG-diacrylate with lithium phenyl-2, 4, 6-trimethylbenzoylphosphinate: polymerization rate and cytocompatibility. *Biomaterials* 30, 6702-6707 (2009).
30. Darley, W. M., Volcani, B. Role of silicon in diatom metabolism: a silicon requirement for deoxyribonucleic acid synthesis in the diatom *Cylindrotheca fusiformis* Reimann and Lewin. *Exp. Cell Res.* 58, 334-342 (1969).
31. Vignolini, S., Moyroud, E., Glover, B. J., Steiner, U. Analysing photonic structures in plants. *J. R. Soc. Interface* 10, 20130394 (2013).
32. Ishimaru, A. *Wave propagation and scattering in random media*. (John Wiley & Sons, 1999).
33. Wiersma, D. S., Lagendijk, A. Light diffusion with gain and random lasers. *Phys. Rev. E* 54, 4256 (1996).
34. Vera, M., Durian, D. J. Angular distribution of diffusely transmitted light. *Phys. Rev. E* 53, 3215 (1996).
35. Syurik, J., Jacucci, G., Onelli, O. D., Hölscher, H., Vignolini, S. Bio-inspired highly scattering networks via polymer phase separation. *Adv. Funct. Mater.,* 1706901 (2018).
36. Fang, Q., Boas, D. A. Tetrahedral mesh generation from volumetric binary and grayscale images. *Proceeding of IEEE International Symposium on Biomedical Imaging* (Piscayaway, NJ) vol. 53, pp. 1142-1145.
37. Fang, Q. Mesh-based Monte Carlo method using fast ray-tracing in Plükker coordinates. *Biomed. Opt. Expr.* 1, 165-175 (2010).
38. Jacques, S. L. Optical properties of biological tissues: a review. *Phys Med. Biol.* 58, R37 (2013).
39. Zhu, C., Lee, Y. Determination of biomass dry weight of marine microalgae. *J. Appl. Phycol.* 9, 189-194 (1997).
40. Naumann, T., Çebi, Z., Podola, B., & Melkonian, M. Growing microalgae as aquaculture feeds on twin-layers: a novel solid-state photobioreactor. *J App. Phyc.,* 25, 1413-1420 (2013)
41. Revsbech, N. P., Jørgensen, B. B. Photosynthesis of benthic microflora measured with high spatial-resolution by the oxygen microprofile method-capabilities and limitations of the method. *Limnol. Oceanogr.* 28, 749-756 (1983).
42. Webb, W. L., Newton, M., Starr, D. Carbon dioxide exchange of *Alnus rubra*: a mathematical model. *Oecologia* 17, 281-291 (1974).
43. Truby, R. L., & Lewis, J. A. (2016). Printing soft matter in three dimensions. *Nature,* 540(7633), 371.

The invention claimed is:

1. A method for promoting microalgae growth, the method comprising:
providing an artificial coral structure by:
disposing a printing surface on a movable stage of a 3D bioprinter, the 3D bioprinter comprising a digital micromirror device configured for modulating light from a light source into patterns defined by a plurality of digital masks, projection optics configured for projecting the modulated light onto a focal plane at the printing surface;
contacting the printing surface with at least one bio-ink, wherein the at least one bio-ink comprises a mixture of a pre-polymer material with one or more of cellulose-derived nanocrystals (CNC), and microalgae cells;
projecting modulated light onto the printing surface while moving the stage to fabricate a 3D scaffold by progressively polymerizing:
a first bio-ink comprising a mixture of pre-polymer material and CNC to define layers of skeletal structures having a plurality of pores and cavities and tissue structures having radially-extending projections, wherein the skeletal structures and tissue structures are configured to scatter light within the structures, and
a second bio-ink comprising a mixture of pre-polymer material and microalgae cells onto the skeletal structures and tissue structures;
disposing the artificial coral structure within a cultivation medium; and
exposing the artificial coral structure to photosynthesis-inducing radiation.

2. The method of claim 1, wherein the first bio-ink further comprises a photoinitiator.

3. The method of claim 2, wherein the first bio-ink further comprises artificial seawater.

4. The method of claim 2, wherein the first bio-ink further comprises a dye configured to limit penetration of polymerizing light into the mixture.

5. The method of claim 2, wherein the pre-polymer material comprises one or more of polyethylene glycol diacrylate (PEGDA) and gelatin methacrylate (GelMA).

6. The method of claim 1, wherein the skeletal structures comprise corallite-shaped functional units tuned to scatter photosynthesis-inducing light.

7. The method of claim 6, wherein the radially-extending projections are disposed around a periphery of the corallite-shaped functional units.

8. The method of claim 1, wherein the plurality of digital masks is generated from slices of microscopic images of natural coral skeletons and tissues.

9. The method of claim 8, wherein the microscopic images are generated using optical coherence tomography (OCT).

10. The method of claim 1, wherein the light source emits light within the visible spectra.

11. The method of claim 1, wherein the light source emits lights at 405 nm.

12. The method of claim 1, wherein the microalgae cells comprise one or more of *Marinichlorella kaistiae, Symbiodinium* sp., and *Thalassiosira pseudonana*.

13. An artificial structure for promoting microalgae growth, comprising:
a 3D-printed structure formed by:
disposing a printing surface on a movable stage of a 3D bioprinter, the 3D bioprinter comprising a digital micromirror device configured for modulating light from a light source into patterns defined by a plurality of digital masks, projection optics configured for projecting the modulated light onto a focal plane at the printing surface, contacting the printing surface with one or more bio-ink comprising a mixture of a pre-polymer material with one or more of cellulose-derived nanocrystals (CNC), and microalgae cells; and projecting modulated light onto the printing surface while moving the stage to progressively polymerize a first bio-ink comprising a mixture of pre-polymer material and CNC to define layers of skeletal structures having a plurality of pores and cavities and tissue structures having radially-extending projections, wherein the skeletal structures and tissue structures are is configured to scatter light within the structures, and a second bio-ink comprising a mixture of pre-polymer material and microalgae cells onto the skeletal structures and tissue structures.

14. The artificial structure of claim 13, wherein the first bio-ink further comprises a photoinitiator.

15. The artificial structure of claim 14, wherein the first bio-ink further comprises artificial seawater.

16. The artificial structure of claim 14, wherein the first bio-ink further comprises a dye configured to limit penetration of polymerizing light into the mixture.

17. The artificial structure of claim 14, wherein the pre-polymer material comprises one or more of polyethylene glycol diacrylate (PEGDA) and gelatin methacrylate (GelMA).

18. The artificial structure of claim 13, wherein the skeletal structures comprise corallite-shaped functional units tuned to scatter photosynthesis-inducing light.

19. The artificial structure of claim 18, wherein the radially-extending projections are disposed around a periphery of the corallite-shaped functional units.

20. The artificial structure of claim 13, wherein the plurality of digital masks is generated from slices of microscopic images of natural coral skeletons and tissues.

21. The artificial structure of claim 20, wherein the microscopic images are generated using optical coherence tomography (OCT).

22. The artificial structure of claim 13, wherein the light source emits light within the visible spectra.

23. The artificial structure of claim 13, wherein the light source emits lights at 405 nm.

24. The artificial structure of claim 13, wherein the microalgae cells comprise one or more of *Marinichlorella kaistiae, Symbiodinium* sp., and *Thalassiosira pseudonana*.

* * * * *